United States Patent [19]

Papadofrangakis et al.

[11] 4,217,909
[45] Aug. 19, 1980

[54] DIRECTIONAL DETECTION OF BLOOD VELOCITIES IN AN ULTRASOUND SYSTEM

[75] Inventors: Emmanuel Papadofrangakis, Schenectady; William E. Engeler, Scotia, both of N.Y.

[73] Assignee: General Electric Company, Schenectady, N.Y.

[21] Appl. No.: 936,111

[22] Filed: Aug. 23, 1978

[51] Int. Cl.$^2$ ............................................. A61B 5/02
[52] U.S. Cl. ............................. 128/663; 73/861.25; 73/602
[58] Field of Search ................................ 128/660–663; 73/194 A, 618, 602

[56] References Cited

U.S. PATENT DOCUMENTS

| | | | |
|---|---|---|---|
| 3,939,707 | 2/1976 | Kossoff | 128/663 |
| 3,953,823 | 4/1976 | Katakura | 128/663 |
| 4,030,062 | 6/1977 | Diehl et al. | 367/103 |
| 4,062,237 | 12/1977 | Fox | 128/663 |
| 4,070,905 | 1/1978 | Kossoff | 340/1 R |
| 4,103,679 | 8/1978 | Aronson | 128/663 |
| 4,109,642 | 8/1978 | Reid et al. | 128/663 |
| 4,141,347 | 2/1979 | Green et al. | 128/663 |
| 4,154,113 | 5/1979 | Engeler | 128/660 |

OTHER PUBLICATIONS

Vogel, S. et al., "The Use of the Doppler Ultrasonic Flowmeter in the Transcutaneous and Intraoperative Measurement of Coronary Artery Blood Flow," Conf: Proc. of the 2d Europ. Cong. on UTS in Med., Munich, Ger. May 12–16, 1975, pp. 169–173.

Baker, D. W., "Pulsed Uts Doppler Blood Flow Sensing," IEEE Trans. SIUS, vol. 17, #3, Jul. 1970, pp. 170–185.

Peronneau, P. et al., "Doppler Ultrasound Pulsed Blood Flowmeter" Onde Electr., vol. 50, fasc. 5, pp. 369–384, May 1970.

*Primary Examiner*—Robert W. Michell
*Assistant Examiner*—Francis J. Jaworski
*Attorney, Agent, or Firm*—Donald R. Campbell; James C. Davis; Marvin Snyder

[57] ABSTRACT

The velocity and direction of the flow of blood and similar liquids, toward or away from the transducer, are measured by coherent demodulation of the received echoes in two quadrature components and subsequent real time processing by a complex Fourier transform processor. A distribution of Doppler frequency shifts and bidirectional velocities are detected and displayed. The preferred embodiment is a duplex imaging system with a sector scanner into which a Doppler modality is incorporated with little added complexity.

7 Claims, 8 Drawing Figures

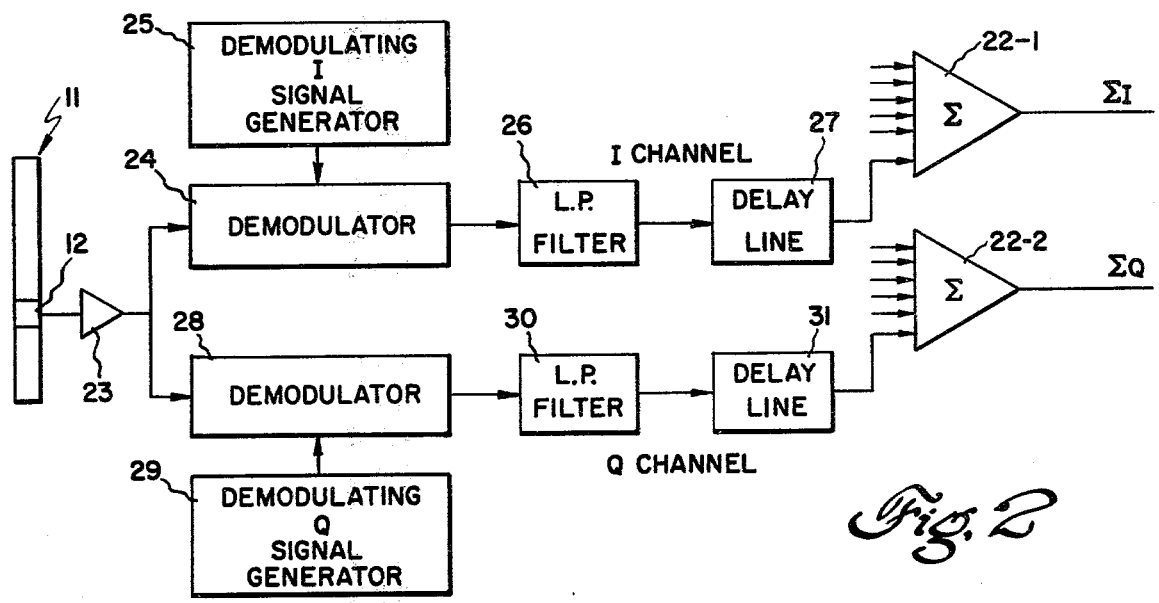
Fig. 2
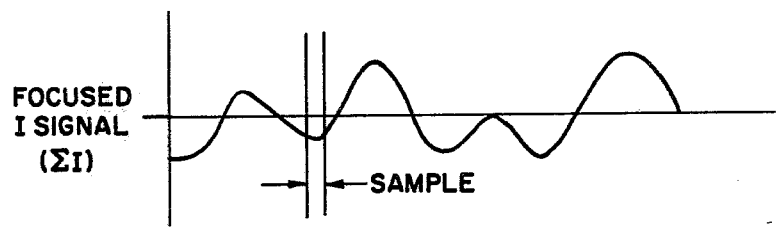
Fig. 6a FOCUSED I SIGNAL (ΣI) — SAMPLE
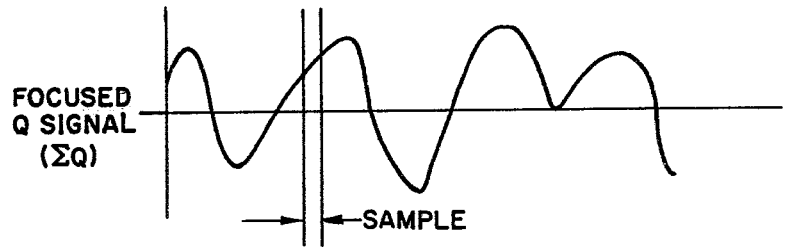
Fig. 6b FOCUSED Q SIGNAL (ΣQ) — SAMPLE
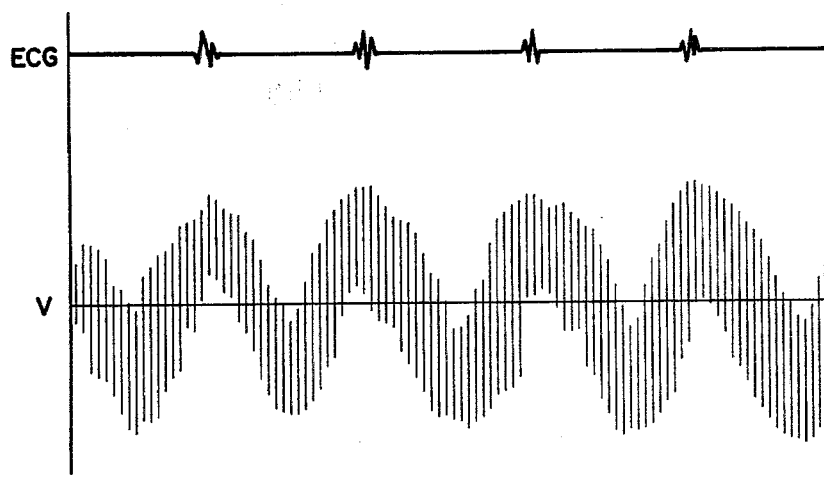
Fig. 7

DIRECTIONAL DETECTION OF BLOOD VELOCITIES IN AN ULTRASOUND SYSTEM

BACKGROUND OF THE INVENTION

This invention relates to a method and ultrasound apparatus for measuring the velocity of blood flow and especially to bidirectional velocity measurement in a system having quadrature echo signal demodulation.

Blood velocity can be detected by measuring the Doppler shifts in frequency imparted to ultrasound by reflection from moving red blood cells. Physicians employing Doppler methods for diagnostic purposes are interested not only in estimating velocity but also in determining whether blood flow is taking place towards or away from the ultrasonic transducer. This need for bidirectional velocity measurement of blood flow has become well accepted, particularly since it was possible to prove that in certain cases, a forward as well as reverse blood flow may simultaneously take place across a given section of the human circulatory system.

Directional velocity capability in prior art systems has been provided by synchronously detecting the echoes in two quadrature channels to obtain both real and complex vectors of the Doppler shifted frequencies. Echo signals from the two channels have been processed in a number of different ways to allow directional flow waveforms to be displayed. Signal analysis in the time domain has been used as a direction resolving technique; using this technique flow direction is determined from which of the processed echo signals leads in time, and this particular signal is then switched on for analysis and display. The method is susceptible to switching artifacts.

Signal analysis in the phase domain has also been proposed as a method of separating from each other forward and reverse flow components. This method relies on phase shifting by 90° signals in each of the quadrature channels and appropriately summing cross terms to implement the mathematical separation of forward and receding flow components. In practice, deviations from the ideal 90° phase shifts required often produces cross talk betwen forward and reverse channels.

Most Doppler units available at present, however, do not employ quadrature channels and utilize a zero-crossing technique to convert the flow velocity and its direction to a proportional positive or negative analog voltage suitable for display. This technique produces a voltage proportional to the mean velocity in the same volume of blood insonified by the ultrasound beam. For some applications, this is all that is necessary, but often it is desirable to visualize the spectral distribution of velocities present in the sample volume.

SUMMARY OF THE INVENTION

An instrument and method for directional velocity measurement of the flow of blood and similar liquids are realized by quadrature ultrasound echo demodulation and spectrum analysis by a complex Fourier transform processor. The system has at the minimum at least one transducer element which is excited to generate pulses of ultrasound with a given emission frequency that insonify a chosen sample volume in the object being examined. The receiver has in-phase and quadrature channels with provision for demodulating the echo signals with phase quadrature emission frequency references and for processing the demodulated signals to produce a focused in-phase (I) signal and a focused quadrature (Q) signal. A range gate extracts a pair of analog samples from the focused signals after every pulse transmission at a time corresponding to reception of backscattered echoes from the sample volume, and a Doppler processor embodying a complex arithmetic implementation of the Fourier transform computes from sets of analog samples the magnitude and sign of a distribution of frequency shifts relative to the emission frequency, which corresponds to the bidirectional velocity distribution in the sample volume. The Doppler processor is preferably a digital Fast Fourier Transform processor which operates in real time.

The preferred embodiment is a duplex imaging system having a B-scan imaging and Doppler orientation mode and subsequent Doppler mode, and is an electronically steered beam single-sector scanner with an incorporated Doppler modality. The system utilizes a common transducer array in both the imaging and the Doppler modes. The focused in-phase and quadrature signals are combined to generate a resultant signal which is fed to the B-scan display device. A sample volume for Doppler interrogation is identified on the image, and narrow bandwidth ultrasound pulses are then transmitted along the scan line intersecting the sample volume and the echo signals are coherently demodulated and dynamically focused as for imaging. The Doppler subsystem extracts analog samples from the focused I and Q signals and has either a block transform mode in which exclusive sets of analog samples are spectrum analyzed or a sliding transform mode in which overlapping sets of analog samples are spectrum analyzed. The FFT processor generates a distribution of frequency shifts or velocities of which half are for flow toward and half for flow away from the transducer. The Doppler display prints out the bidirectional velocity distribution vs. time with which is multiplexed an ECG signal, and there can also be an oscilloscope so the user may observe the velocity variation in real time.

BRIEF DESCRIPTION OF THE DRAWINGS

FIG. 2 is a block diagram of a receiving channel giving in more detail the in-phase (I) and quadrature (Q) signal processing channels;

FIGS. 6a and 6b are waveform diagrams of the focused I and Q echo signals which are the inputs to the Doppler subsystem; and FIG. 7 is a typical velocity vs. time display for the Doppler mode and an optional ECG reference signal.

DESCRIPTION OF THE PREFERRED EMBODIMENTS

Figure 1:
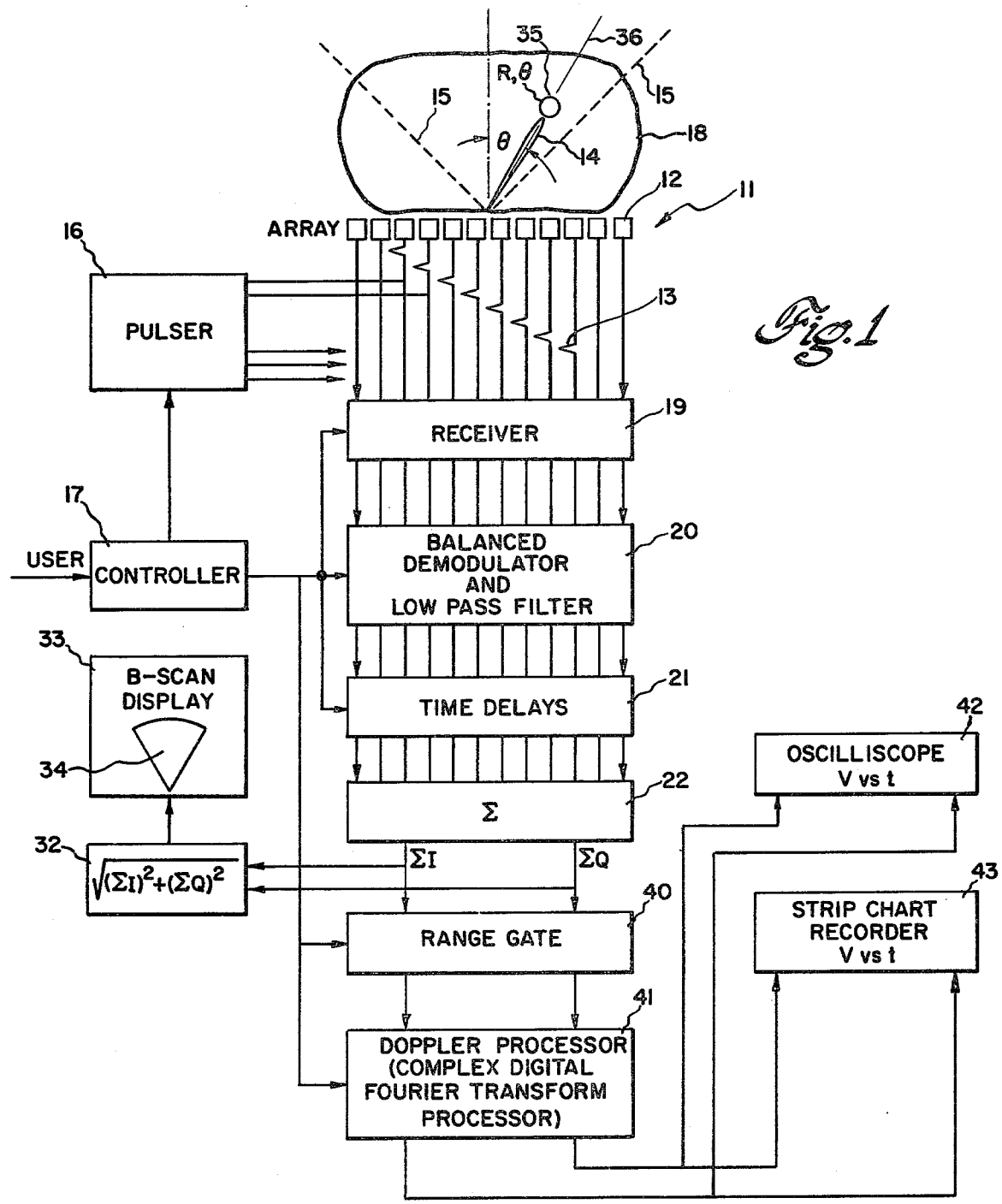
FIG. 1 is a simplified block diagram of a duplex ultrasonic imaging system with capability for bidirectional velocity measurement in the Doppler modality.

The duplex ultrasonic imaging system in FIG. 1 has both B-scan and Doppler modes of operation and in the latter modality provides real time directional blood velocity information from a preselected point in the blood stream using a Fourier transform processor to compute the velocity distribution present in a small sample volume. The Doppler processor is incorporated in an imaging system which offers the physician a visual orientation facility, and employing the image as a guide he can select to interrogate for Doppler almost any point in the field of view of the instrument. A common transducer array is provided for both imaging and Doppler examinations and the motivation behind this approach is the accuracy that can be obtained in orientation and the resulting system simplicity. Another feature important from the standpoint of this invention is that the quadrature echo demodulation in the signal processing necessary for imaging has a dual function to implement the Doppler modality. An ultrasonic imaging system which includes coherent demodulation of echo signals followed by time delay and coherent summation of the demodulated signals is described in a copending application by that title, Ser. No. 908,908 filed on May 24, 1978, now U.S. Pat. No. 4,155,260 W. E. Engler and J. J. Tiemann, assigned to the same assignee as this invention. The echo processing channels of the duplex system can be the same as in that application, but are described only to the extent needed to understand the present invention. Before proceeding further, principles of beam formation and echo signal processing in steered beam or phased array imagers are reviewed.

Common linear transducer array 11 in FIG. 1 is comprised of a large number of piezoelectric transducer elements 12 which are energized by excitation pulses 13 in a linear time sequence to form an ultrasound beam 14 and direct the beam in a preselected azimuth direction to transmit a pulse of ultrasound. In order to steer the beam electronically to an angle $\theta$ degrees from the normal to the array longitudinal axis, a time delay increment is added successively to each signal as one moves down the array from one end to the other to exactly compensate for the propagation path time delay differences that exist under plane wave (Fraunhofer) conditions. By progressively changing the time delay between successive excitation pulses, the angle on one side of the normal is changed by increments, and to form an acoustic beam at the other side of the normal, the timing of excitation pulses 13 is reversed so that the right-hand transducer is energized first and the left-hand transducer is energized last. Only the center portion of the array is used for transmit but the entire array is used for receive. A total sector scan angle indicated by dashed lines 15 is approximately 60° to 90°. Echoes returning from targets in the direction of the transmitted beam arrive at the transducer elements at different times necessitating relative delaying of the received echo signals by different amounts so that all the signals from a given point target are summed simultaneously by all elements of the array. The time delays of the individual echo signals are the same as during transmission to compensate for acoustic path propagation delay differences, and these are referred to as being steering time delays or simply steering delays. Every receiving channel also electronically and dynamically focuses a received echo to compensate for the propagation path time delay differences from the focal point to the varying individual array element positions. The receiving focus can be dynamically changed to track the range from which echoes are being received during the echo reception period by a multi-step approximation. This sector scanner features fine and coarse step focusing, where fine focusing is achieved by dynamically phased coherent demodulation and coarse focusing is accomplished as in beam steering by channel-to-channel electronic signal delay differences. Electronically variable delay lines provide the steering and focusing time delays. To effect coherent summation of the contributions from all receive elements, the delayed echo signals from the inphase (I) and quadrature (Q) receiving channels are fed to summing amplifiers at the output of which are focused I and Q echo signals. Further processing of the focused signals generates the B-scan display data.

The duplex imaging system in FIG. 1 is a real time single-sector steered beam scanner into which is incorporated a Doppler modality for real time bidirectional blood flow velocity measurement. There are two modes of operation of the duplex imager system for velocity measurements: (a) the B-scan imaging and Doppler orientation mode and (b) the Doppler processing and display mode. The latter modality is always subsequent to the former and the two are never simultaneous. Common linear transducer array 11 has a larger interelement spacing for receive than for transmit to yield a wide aperture system with low side lobe artifacts using a minimum number of relatively expensive receiver channels. The transmit array is at the center of a larger receive array (elements in the center may function dually as transmit and receive elements), and the transmit elements are associated with a pulser 16 capable of generating single impulses for B-scan operation so as to produce wide bandwidth ultrasound pulses, and multiple impulses for Doppler operation having a frequency equal to the required emission frequency so as to generate narrow bandwidth ultrasound pulses. The repetition frequency of multiple impulse excitation is variable and has high, intermediate, and low settings selected by a controller 17 with user inputs. For further information on satisfying the conflicting bandwidth requirements, reference may be made to concurrently filed allowed application Ser. No. 936,115, E. Papadofrangakis, J. A. Fakiris, and W. E. Engeler, "Duplex Ultrasonic Imaging System with Repetitive Excitation of Common Transducer in Doppler Modality," assigned to the assignee of this invention.

During successive transmission periods of the B-scan mode, pulser 16 generates a series of excitation impulses 13, one per transmitter element, with a time delay between successive impulses that is incremented from one transmission period to the next to thereby transmit wide bandwidth pulses of ultrasound along many different scan lines covering the region of a body 18 being examined. During alternate reception periods, the received echo signals caused by energy echoing from various body structures and detected by receive elements 12 in common array 11 are individually amplified and fed to echo processing channels. The major components of the receiving channels, which feature the use of base band signal processing to achieve good lateral resolution while greatly reducing the required time delay accuracy and instead requiring more easily achievable phase focusing accuracy, have as major components a receiver 19 for each channel, a balanced demodulator and low pass filter 20, a time delay device 21, and a pair of summers 22.

Referring to FIG. 2, the I and Q processing channels for the echo signal generated by a single receive element 12 are depicted in greater detail. The echo signal passes through a preamplifier 23 to an I channel demodulator 24 where it is mixed with a demodulating signal from generator 25 which has a fundamental frequency equal to the resonant frequency of the transducer element or equal to the ultrasound emission frequency. The demodulating reference signal further has a phase determined by the path length difference to the object point under examination. The demodulated signal is passed through a low pass filter 26 to recover the envelope and is then fed to a delay line 27 which is preprogrammed with the steering delays and, in the situation where the path lengths differ sufficiently, a coarse focusing delay proportional to the path length difference. The delayed, focused demodulated signal is fed to summing amplifier 22-1 where it is coherently summed with all the other I channel delayed demodulated signals to give the focused in-phase signal $\Sigma I$. The demodulated signal utilized in each of the Q channels is set to be in phase quadrature relationship with respect to the demodulating signal in the respective I channels. The echo signal is fed in parallel to demodulator 28 and mixed with a phase quadrature emission frequency reference from generator 29 which is further set lagging in phase with respect to the echo signal by the same phase displacement existing in connection with the echo and demodulating signals in the I channel. The quadrature demodulated signal similarly is passed through low pass filter 30 to recover the envelope, is steered and time delay focused in delay line 31, and then fed to summing amplifier 22-2 to be coherently summed with the delayed, focused demodulated signals from other Q channels to yield the focused quadrature signal $\Sigma Q$.

In practice, three receiver system parameters are varying during the course of an echo reception period, these being the time delay between elements, the reference signal of the balanced demodulators, and also the receive aperture width. The outermost receiving channels (FIG. 1) are blanked progressively at shorter ranges to reduce the receive aperture by steps and realize improved lateral resolution near the skin. For B-scan operation, the summed and focused I and Q signals are further processed at 32 to derive a resultant signal obtained by squaring the I and Q signals, adding together the squared signals and taking the square root of the sum. The resultant is the video signal and it is post-processed to improve the image before being fed to cathode ray tube 33 as the Z control or to control the electron beam intensity. Sector-shaped image 34 is built up radial scan line by radial scan line as the transmitted beam direction is changed incrementally, and is a two-dimensional picture of a planar slice through the body which is displayed in real time. The Doppler orientation mode involves visual observation of B-scan image 34 by the physician to identify a relatively small sample volume within the heart or closeby great arterial vessels through which the velocity of blood flow is to be measured. A suitable landmark on the image delineates the Doppler examination region, such as means for illuminating the beam direction through the sample volume and an illuminated range cursor. Assume for instance that a sample volume 35 is being examined (top of FIG. 1) which is along scan line 36 at an angle $\theta$ to the normal and which has a range R.

In the Doppler mode of operation, system controller 17 is set by the user such that narrow bandwidth pulses of ultrasound are transmitted only along the chosen scan line intersecting the sample volume, and range gating is employed to sample echoes from the desired depth and detect velocity patterns at specific locations. Repetitive pulsing of the transmitter elements at a frequency equal to the required emission frequency causes the response bandwidth of the transducer to be narrowed. By an appropriate timing of the beginning of the multiple pulsing of each element (time delay increments are the same as for single impulse excitation), the transmitted ultrasound beam is steered to a certain direction or can be focused at a certain point in space. Another feature of the Doppler modality transducer excitation is variable repetition intervals for the multiple excitation in order to be able to adequately sample, at various ranges, backscattered echoes from slow as well as fast moving blood cells. The instrument being described has pulse repetition frequency (PRF) settings of 4 KHz, 8 KHz, and 16 KHz. For high values of velocity flow in sample volumes at close ranges, detection is accomplished by using a 16 KHz PRF. The velocity resolution is relatively poor. Superior velocity resolution at low flow velocities and long ranges is achieved by the 4 KHz PRF. To provide additional flexibility in the choice variable to the user, there is an intermediate setting of 8 KHz PRF. The chosen PRF (ultrasound pulse repetition frequency) values in the Doppler mode are considerably higher than those provided in imaging, and the transmitter subsystem is capable of providing appropriate excitation intervals for both modes of operation.

Figure 3:
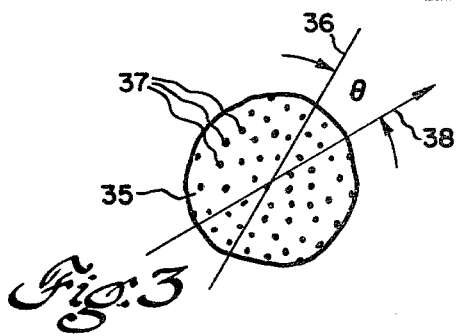
FIGS. 3 and 4 are enlarged views of a sample volume of blood showing in FIG. 3 a velocity vector at an angle $\theta$ to the transmitted acoustic beam and in FIG. 4 a sample volume with turbulent flow.
Figure 4:
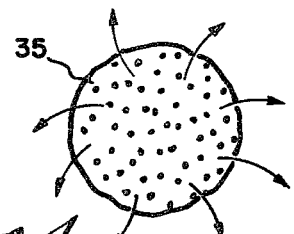

FIG. 3 is an enlarged view of sample volume 35 and of red blood cells 37 in the blood stream which are very small (about 8 microns in diameter) as compared to the ultrasound wavelength. Red blood cells 37 move with a certain mean velocity indicated by arrow 38 that is at an angle $\theta$ to the direction of the incident energy along scan line 36. Echoes backscattered from the red blood cells are frequency shifted by an amount proportional to the frequency of the incident wave and the velocity of blood flow. Movement of red blood cells through the sample volume toward the transducer array compresses the wavelength of the reflected wave, increasing the frequency; movement of red blood cells away from the transducer array lengthens the wavelength of the reflected wave, decreasing the frequency. The instrument measures only the component of mean velocity 38 in the direction of the transmitted ultrasound beam defined by scan line 36. The formula relating Doppler frequency shift and velocity is $$\Delta f = 2 f_o v \cos \theta / c \quad (1)$$

where $\Delta f$ = frequency shift, $f_o$ = ultrasound emission frequency, v = mean velocity of blood flow, and c = speed of sound in tissue (1450 m/sec). The ultrasound emission frequency for cardiac scanning is in the order of 2–5 MHz. The range of human blood velocities is known and Doppler shifts are in the audio spectrum of about 0.2–8 KHz. The red blood cell population of sample volume 35 is constantly changing and it is necessary to get a number of samples of frequency shifted echoes in order to calculate an accurate value of velocity. Red blood cells moving past the sample volume backscatter ultrasonic energy containing a spectrum of Doppler frequencies, and these correspond to the distribution of velocities present in the sampled region. Mean velocity can be calculated by averaging the components of the distribution. Another factor is that blood flow may be turbulent as shown in FIG. 4 and the velocity then is in many directions. Knowledge of the distribution of bidirectional velocities improves the accuracy of detecting turbulent blood flow. The dimensions of sample volume 35 are made relatively small, such as a 2 mm diameter, because then a more valid representation of velocity at a specific point is obtained. The present duplex system acquires multiple samples of frequency shifted echoes in the Doppler mode for each velocity determination, i.e., there are multiple pulse transmissions and in each case the echo signals are focused and samples are gated to the Doppler processor.

Directional detection of blood velocities is based on synchronous demodulation of the received echoes in two quadrature components as just described and subsequent processing by a complex Fourier transform processor. By properly selecting the Doppler processor, bidirectional velocity measurements of the flow of blood and similar liquids are achieved in real time. In the Doppler mode of operation, the echo signals are processed through the quadrature receiving channels and electronically steered and dynamically focused in exactly the same manner as for B-scam imaging with the exception that the summed and focused I and Q signals are fed directly to the Doppler system without generating their resultant. The focused in-phase and quadrature signals are sampled at a specific time after each transducer excitation interval which corresponds to the time taken for the ultrasonic signal to return to the transducer from range R. A range gate 40 is opened by controller 17 for a relatively short interval at a time corresponding to reception of echoes backscattered from the sample volume and extracts a pair of analog samples in parallel. Doppler processor 41 embodies a complex arithmetic implementation of the Fourier transform and derives from sets of pairs of analog samples, the magnitude and sign of the frequency shifts of echoes with respect to the emission frequency, and therefore the flow velocity and its direction. The Doppler processor is preferably a real time digital Fast Fourier Transform (FFT) processor. Full spectral analysis is a powerful method using the entire power spectrum of Doppler shifted components that correspond to the red blood cell velocity distribution in the sample volume. The power spectrum contains all the available information concerning the flow of blood through the transducer beam. The output spectral components can be averaged in a mathematically correct way to obtain accurate mean frequency estimates. Knowledge of the speed of sound in tissue and the emission frequency of ultrasound pulses provides the additional parameters necessary for a mean velocity reading. It is best, however, to compute a distribution of frequency shifts and display a distribution of bidirectional velocities.

The duplex imaging system has two types of Doppler mode display devices for the velocity information. The distribution of Doppler frequencies are first displayed on an oscilloscope 42 so that the user can observe their variation in real time. A hard copy of the evolution of the velocity distribution with time is printed up by a strip chart recorder 43. The recorder plots the information at a rate selected at the start, and most of the display period is taken up by the Doppler information with a smaller portion reserved for a multiplexed ECG signal. The latter provides a time reference for events occurring during the course of a heart cycle.

Figure 5:
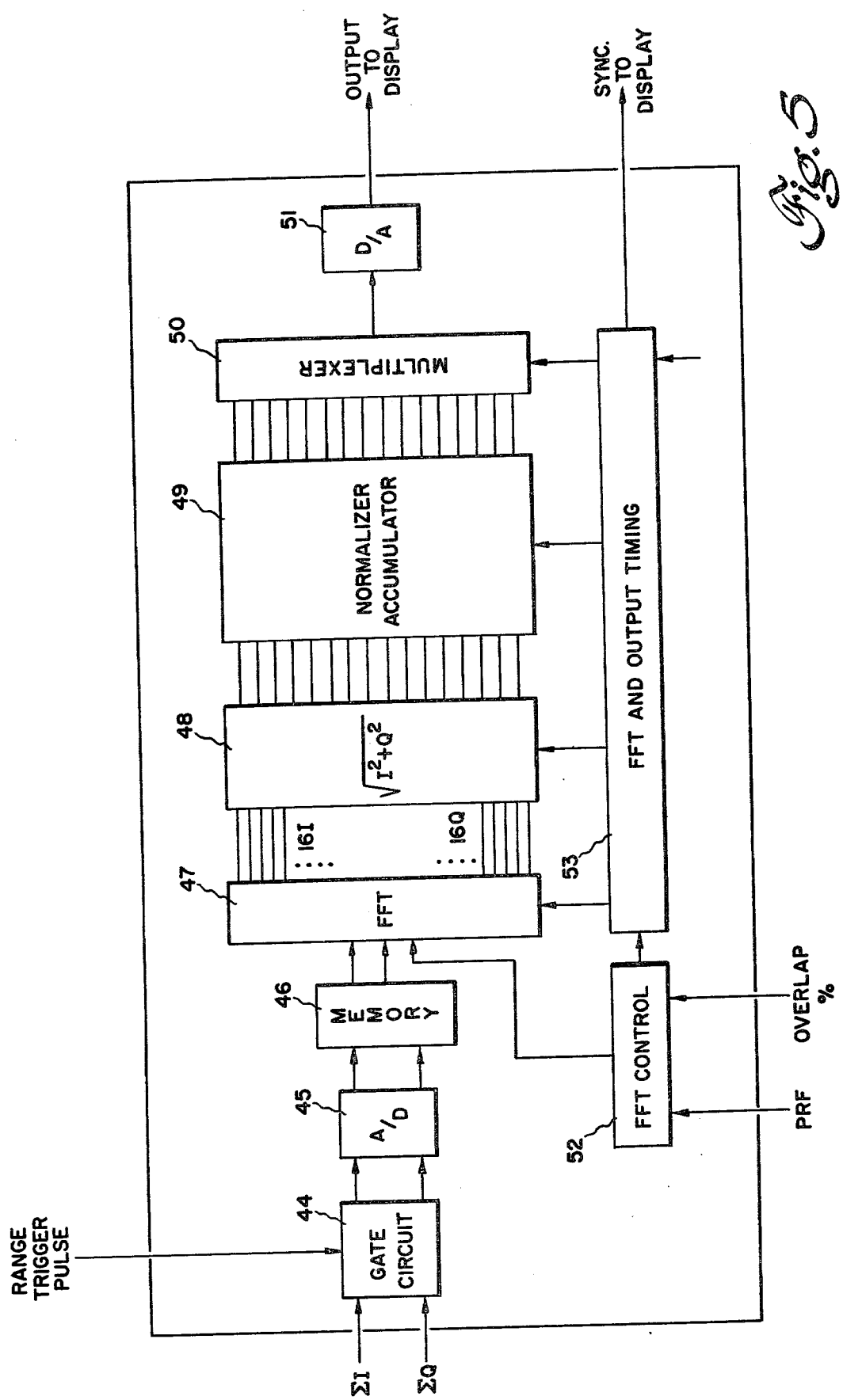
FIG. 5 is a block diagram of the Doppler subsystem.

FIG. 5 is a block diagram of the preferred embodiment of the Doppler subsystem. This subsystem extracts a Doppler frequency spectrum from sixteen focused in-phase and quadrature signals, computes the power spectrum and generates an analog output that represents sixteen Doppler frequencies. Half of these frequencies correspond to positive Doppler shifts (forward flow) and the other half to negative shifts (receding flow). The processor operates in real time with the system running at pulse repetition frequencies of 4 KHz, 8 KHz, and 16 KHz. When processing time is available, particularly at the higher PRF's, the processor integrates several spectra before reporting results. The processor can operate on data samples in one of two ways resulting in either a block or a sliding transform.

Gate or sampling circuit 44 corresponds to range gate 40 and extracts a sample of the focused I and Q signals (ΣI and ΣQ) from the time delay subsystem at a time corresponding to the user selected target range. As was explained, at the instant of Doppler sampling the values of aperture width, demodulator reference phase, and time delay are automatically those required to focus at range R. Although the parameters vary during the course of a pulse repetition interval, they are always the same at the selected instance of sampling from one repetition interval to the next. Typical focused I and Q signals are illustrated in FIGS. 6a and 6b. The sampling interval is very short, such as 0.1 microseconds, as compared with the time duration of the ultrasound pulse to realize velocity measurements with maximum sensitivity at a specific point in the blood stream. Upon the occurrence of a range trigger pulse (FIG. 5), gate circuit 44 passes a pair of analog samples to analog-to-digital converter 45 and the pairs of digitized samples are stored in a memory 46. Doppler processor 47 features a digital implementation of a sixteen-point real time Fast Fourier Transform. The number of transform points is determined by the minimum desirable spectral resolution and a tradeoff of range and velocity discrimination. FFT 47 is constructed with eight CE chips such as are disclosed and claimed in U.S. Pat. No. 4,020,334, N. R. Powell and J. M. Irwin, "Integrated Arithmetic Unit for Computing Some Indexed Products," assigned to the assignee of this invention, the disclosure of which is incorporated herein by reference. These CE chips provide complex arithmetic for a sixteen-point digital FFT based on radix 4 algorithm. The digital FFT computation gives an ordered output frequency spectrum comprising sixteen frequency bins, half of which correspond to positive Doppler shifts and the other half to negative shifts. An output spectrum can be calculated once sixteen I and sixteen Q samples from sixteen consecutive echo returns are accumulated in memory 46. These samples are Fourier transformed to produce sixteen real and sixteen imaginary coefficients, and the power spectrum is obtained by squaring and adding the coefficients on a 1:1 basis. Movement of the red blood cells causes rotation of an I-Q phasor in a unit circle. The rate of rotation indicates velocity, direction of rotation gives flow sense. It is a property of the Discrete Fourier Transform (DFT) that contradirected velocities produce complex output numbers corresponding to different velocity bins. In this way, a complex arithmetic Fourier transform permits a separation of the Doppler spectra for forward or receding flow.

The outputs of the FFT processor 47 are sixteen I and sixteen Q signals representing frequency shifts, and sixteen resultant signals are generated for display in circuit 48 in the same fashion as for the B-scan display by squaring corresponding I and Q signals, adding the squares and taking the square root of the sum. The sixteen resultant signals, half for forward flow and half for receding flow, are fed to an accumulator normalizer 49 for presentation to the display either in block transform mode or sliding transform mode. In the first exclusive sets of analog sample pairs are analyzed, i.e., pulse-echo cycles 1-16, 17-33, etc. In the latter mode overlapping sets of analog sample pairs are analyzed, i.e., pulse-echo cycles 1-16, 4-20, 8-24, etc. Video output data passes through a multiplexer 50 where it is multiplexed with the ECG signal, and is then fed to a digital-to-analog converter 51 to generate the output data.

Doppler subsystem control units 52 and 53 are illustrated without a full showing of the input commands from controller 17. Block 52 is the FFT control and its inputs are a transform slide number command and a velocity scaling command, and block 52 is FFT and output timing circuitry.

At each instant in time, the Doppler processor reports the ultrasound power spectra backscattered from the sample volume, and this corresponds to the velocity distribution in the sample volume. The distribution contains eight positive and eight negative readings, and one may average the velocity components present in the sample volume and display a mean velocity reading. Alternatively, the entire distribution can be displayed, and the latter approach is preferable in situations of turbulent flow. A typical plot of bidirectional blood flow velocities vs. time, with a distribution of velocities at every time coordinate, such as is printed out by strip chart recorder 43 (FIG. 1), is given in FIG. 7. A multiplexed ECG signal to provide a heart cycle time reference is also illustrated. The velocity scale for strip chart recorder 43 is coordinated with the selection of pulse repetition frequency that the system will use. The selection procedure is to start with the maximum velocity, and therefore maximum PRF, consistent with the selected range, and then decrease it in binary steps if the observed result is less than one-half cycle. This procedure avoids aliasing the Doppler velocity.

It is not essential to the invention to have a transducer array and a multiple channel receiver, and an ultrasound instrument for bidirectional velocity measurement of the flow of blood or similar liquids may have only one transducer element with I and Q signal processing channels such as is shown in FIG. 2. Synchronous demodulation of the echo signals with phase quadrature emission frequency references is an essential feature of the signal processing, but phase focusing as previously described is not essential. Likewise, the Doppler instrument can be built as a separate unit and need not be part of a duplex system with B-scan imaging capability. In either case, this ultrasound technique is a strictly non-invasive, nontraumatic method for measuring bidirectional blood velocity.

While the invention has been particularly shown and described with reference to several preferred embodiments thereof, it will be understood by those skilled in the art that various changes in form and details may be made therein without departing from the spirit and scope of the invention.

The invention claimed is:

1. A steered beam ultrasound instrument for measuring the velocity of flow of blood and similar liquids comprising:
    a transducer array having plural electroacoustic transducer elements for transmitting pulses of ultrasound with a preselected emission frequency and for generating received echo signals,
    transmitter means for sequentially exciting selected transducer elements with an element-to-element timing to generate a narrow bandwidth ultrasound pulse that propagates along a chosen radial scan line and insonifies a sample volume in the object being examined through which flow velocity toward and away from the array is being measured,
    a multichannel receiver means for coherently demodulating said echo signals with phase quadrature emission frequency references and for time delaying and summing the demodulated signals to produce a focused in-phase signal and a focused quadrature signal,
    a range gate for extracting a pair of analog samples in parallel from said focused in-phase and quadrature signals after every pulse transmission at a time corresponding to reception of echoes backscattered from the sample volume,
    a digital complex Fourier transform processor for repeatedly and in real time deriving from sets of said pairs of analog samples the magnitude and sign of the frequency shift of echoes with respect to the emission frequency and therefore the flow velocity and direction, and
    display means for visually displaying bidirectional velocity as a function of time.

2. The ultrasound instrument of claim 1 wherein said complex Fourier transform processor is a sixteen-point Fast Fourier Transform processor which produces a distribution of frequency shifts and velocities of which half are for flow toward the array and half away from the array, and wherein said display means displays a distribution of velocities at every time coordinate.

3. A duplex ultrasonic imaging system having a B-scan and Doppler orientation mode of operation and a subsequent Doppler mode of operation comprising:
    a common transducer array for both modes comprised of plural piezoelectric elements for transmitting pulses of ultrasound with a preselected emission frequency and for generating received echo signals,
    means for exciting selected array elements during B-scan operation to sequentially produce ultrasound pulses that are transmitted along different scan lines to perform a scan of a region being examined,
    means for coherently demodulating said echo signals using phase quadrature emission frequency references and for time delaying and summing the demodulated signals to produce a focused in-phase signal and a focused quadrature signal,
    means for deriving a resultant signal from said focused in-phase and quadrature signals, and a B-scan display for displaying said resultant signals as a visual image of the insonified region,
    means for exciting selected array elements during Doppler operation to sequentially produce ultrasound pulses that are transmitted along a chosen scan line intersecting a sample volume through which the velocity of blood flow toward and away from the array is being measured, the received echoes being coherently demodulated and time delayed and summed by the previously mentioned means to produce focused in-phase and quadrature signals,
    a Doppler subsystem including a range gate for extracting a pair of analog signals in parallel from said focused in-phase and quadrature signals after every pulse transmission at a time corresponding to reception of echoes backscattered from the sample volume, and further including a digital complex Fourier transform processor which operates in real time for deriving from sets of said pairs of analog samples the magnitude and sign of the distribution of frequency shifts of echoes with respect to the emission frequency and therefore the distribution of bidirectional velocities, and Doppler display means for visually displaying bidirectional velocity as a function of time.

4. The duplex system of claim 3 wherein said Doppler display means includes an oscilloscope for displaying the distribution of velocities at every time coordinate and a recorder for printing out the distribution of velocities with which is multiplexed an electrocardiogram signal.

5. A method of bidirectional velocity measurement of the flow of blood and similar liquids using a real time sector-scan imging system with an incorporated Doppler modality comprising the steps of:

exciting a transducer array of piezoelectric elements to sequentially generate pulses of ultrasound that propagate along a selected scan line and insonify a chosen sample volume in the object being examined through which flow velocity toward and away from the array is being measured, and alternately after every pulse transmission detecting received echoes and generating echo signals, processing the echo signals in multiple receiving channels each having an in-phase and a quadrature channel in which the echo signals are coherently demodulated using phase quadrature emission frequency reference signals and dynamically focused and summed to produce focused in-phase and quadrature signals, gating said focused signals for a short interval after every pulse transmission to extact a pair of analog samples representing echoes back-scattered from the sample volume, and analyzing sets of said pairs of analog samples in real time with a digital complex Fast Fourier Transform processor to derive the magnitude and sign of the distribution of frequency shifts of echoes with respect to the emission frequency and therefore the distribution of bidirectional velocities.

6. The method of claim 5 wherein said processor operates in block transform mode and acquires and analyzes exclusive sets of said pairs of analog samples.

7. The method of claim 5 wherein said processor operates in sliding transform mode and acquires and analyzes overlapping sets of said pairs of analog samples.

* * * * *